United States Patent [19]

Cherksey

[11] Patent Number: 5,750,697
[45] Date of Patent: May 12, 1998

[54] MEMBRANE NA⁺ CHANNEL PROTEIN AND RELATED THERAPEUTIC COMPOUNDS

[76] Inventor: Bruce D. Cherksey, 608 Garden St., Hoboken, N.J. 07030

[21] Appl. No.: 916,912

[22] Filed: Jul. 20, 1992

Related U.S. Application Data

[62] Division of Ser. No. 516,626, Apr. 30, 1990, Pat. No. 5,132,296, which is a division of Ser. No. 85,462, Aug. 14, 1987, Pat. No. 4,950,591.

[51] Int. Cl.⁶ .................................................. C07D 241/02
[52] U.S. Cl. .................................... 544/409; 514/85
[58] Field of Search .................... 544/409; 540/554; 514/85

[56] References Cited

U.S. PATENT DOCUMENTS 4,894,376  1/1990  Morad et al. ........................ 544/407
4,895,807  1/1990  Cherksey ............................. 530/395
4,898,729  2/1990  Miller et al. ....................... 514/223.2
4,950,591  8/1990  Cherksey ............................. 435/7
5,132,296  7/1992  Cherksey ............................. 514/57

*Primary Examiner*—Mukund J. Shah
*Assistant Examiner*—Pk Sripada
*Attorney, Agent, or Firm*—Lyon & Lyon LLP

[57] ABSTRACT

A channel protein having a $Na^+/K^+$ selectivity of approximately 100 and capable of affecting $Na^+$ membrane transport is disclosed. Amiloride derivatives, and amiloride gel materials incorporating such derivatives, useful in treating membrane transport, cellular volume and cellular pressure disorders and in isolating the channel protein are also disclosed. These amiloride derivatives may be prepared by mixing the amiloride with an alkanediol in the presence of a base followed by addition of an acid. Use of the channel protein in diagnostic assays and screening assays is described.

8 Claims, 1 Drawing Sheet

MEMBRANE NA⁺ CHANNEL PROTEIN AND RELATED THERAPEUTIC COMPOUNDS

This application is a divisional of application Ser. No. 07/516,626, filed on Apr. 30, 1990, now U.S. Pat. No. 5,132,296, which was a divisional of application Ser. No. 07/085,462, filed Aug. 14, 1987, now U.S. Pat. No. 4,950,591.

BACKGROUND OF THE INVENTION

The ability to control transport of chemical species across cellular membranes is important from a therapeutic standpoint inasmuch as a number of disease conditions, including glaucoma and certain kidney and stomach disorders, are directly related to such transport. In addition, a better understanding of the mechanisms for such transport can be expected to yield improved therapeutic and diagnostic tools.

It is thought that transport of ions, including $Na^+$, across membranes is controlled in part by membrane channel proteins which exist in certain membranes and which act to transport or "channel" ions across such membranes. Only about six or so protein channels have actually been isolated. Epithelial $Na^+$ channel proteins have been discussed by Palmer in *J. Membrane Biol.*, Vol. 96, pp. 97–106 (1987). Agents which selectively block ion transport have been described, as for example amiloride (3,5-diamino-N-(aminoiminomethyl)-6-chloropyrazinecarboxamide). Amiloride is widely thought to interact with a $Na^+/H^+$ exchanger at high concentrations and a $Na^+$ channel protein at much lower concentrations. By utilizing the channel protein binding compound amiloride in affinity gels, it has been shown in investigations relating to the present invention to be possible to isolate and purify the $Na^+$ channel protein. Both the channel protein and the binding compounds and associated affinity gels are useful in therapeutic control of membrane transport or in developing assays related to membrane control.

The full disclosure and claims of applicant's prior copending application, Ser. No. 948,262, now U.S. Pat. No. 4,895,887 is incorporated herein by reference.

SUMMARY OF THE INVENTION

The present invention involves a newly-isolated membrane channel protein which has been found to be related to $Na^+$ transport across cellular membranes. The $Na^+/K^+$ selectivity of the protein is approximately 100. The channel protein has been found in a variety of cell samples including kidney and trachea epithelial cells. Discovery and isolation of this channel protein provides an avenue for regulating ion transport across membranes by utilizing transport blockers which bind to the peptide. Such regulation may also be modulated by the use of $Ca^{++}$, pH or other media adjustments in in vivo or in vitro systems.

It has also been discovered that the channel protein blocking compound amiloride and derivatives thereof may be used to regulate the transport activity of the channel protein by virtue of their ability to bind to the peptide. Such compounds would be useful in oral, ocular, topical or other administration media to correct membrane transport, cellular volume or cellular pressure disorders such as those associated with glaucoma, gastric ulcers, diuresis problems, hypertension, obesity and the like. Preferred blocking compounds include the reaction products of amiloride and alkanediols, particularly ethane-1,2-diol (ethylene glycol), propane-1,3-diol, butane-1,4-diol, pentane-1,5-diol and the like.

The foregoing channel protein blocking compounds may also be covalently bonded to suitable support media, including monosaccharide or polysaccharide support materials such as those commonly used for gel affinity chromatography, to yield materials which are useful in isolating and purifying the channel protein. Bonding of the amiloride molecule to the support media is achieved in a manner which preserves the ability of the amiloride to bind to the peptide channel, and may be achieved using a glycol or other "linker" group. Such "affinity gel" materials are also useful in their own right as therapeutic compounds capable of regulating membrane transport, cellular volume or cellular pressure disorders. The blocking compounds may also be bonded to other useful groups, such as radiolabels or fluorescent labels.

The channel protein is useful in developing diagnostic assays, as for example immunoassays, relating to membrane transport, cellular volume or cellular pressure disorders in appropriate membrane systems. It may also be used in in vitro screening assays to screen large numbers of test compounds for activity in modulating transport, volume and pressure controls in in vivo and in vitro systems.

Thus, in one respect, the present invention relates to a new and useful protein which has been shown to act as a channel for $Na^+$ ions in a variety of naturally-occurring cellular membranes. The protein is useful as an agent for developing diagnostic assays, as for example immunoassays utilizing monoclonal or polyclonal antibodies, which may be directed toward determining, in histopathological samples, the extent to which volume and pressure problems may result from abnormally high or abnormally low presence of the $Na^+$ channel in appropriate membranes. In another aspect, the channel protein is useful as an agent for measuring in vitro the effectiveness of experimental compounds in displacing known blockers of the channel protein, thus furnishing a relatively inexpensive means for screening such compounds for therapeutic transport-modulation activity.

The present invention also provides methods for producing the channel protein. These methods involve the use of new and useful compositions which bind to and/or block the channel protein, including such compositions covalently bonded to appropriate support media including modified polysaccharide support materials derived from, for example, purified agarose, dextran, cellulose or short-chain polysaccharides or monosaccharides such as glucose or dextrose. Such compositions, when bonded to a support structure, are useful in purifying the channel protein from membranal material. In addition, the compositions in their pure and/or support media-bound forms are useful in treating transport-related disorders such as ulcers, diuresis-related disorders, diarrhea, glaucoma, hypertension and obesity.

DETAILED DESCRIPTION

Figure 1:
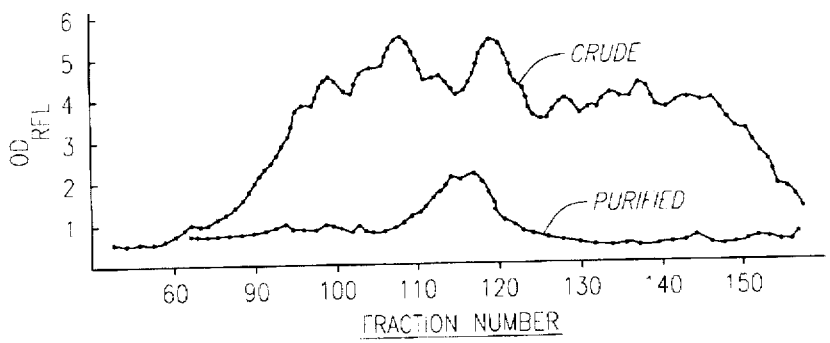
FIG. 1 is a graph depicting gel filtration elution curves for the $Na^+$ channel protein of the present invention, eluted both in crude membranal homogenate and amiloride affinity gel-purified forms.

The diuretic and antihypertensive drug amiloride is known to block cation transport across membranes. Derivatives of the drug have been shown in gel affinity chromatography experiments relating to the present invention to be useful in purifying a membrane protein from bovine kidney cortex and bovine trachea epithelia apical membranes. This protein has been shown to be a membranal "channel protein" which incorporates a $Na^+$ channel, as ascertained from electrical measurements on the purified protein inserted into planar lipid bilayers.

It has been found that glycol adducts of amiloride are particularly useful in the practice of the present invention. Thus, a glycol of from two to six or more carbons may be reacted with amiloride at a pH of about 9 to form a soluble, glycolated amiloride derivative that retains the $Na^+$ channel protein blocking activity of the native amiloride. The glycol portion of the adduct may be used as a "linker group" to bond the amiloride to other materials in a manner which preserves the amiloride activity.

It will be recognized that derivatives of amiloride which exhibit the ability of the native compound to block the $Na^+$ channel protein will also be useful in the practice of the present invention, and may also be used to form the, e.g., glycol adduct compositions and affinity gel preparations described herein. Other derivatizing groups capable of reacting with amiloride in a manner which retains the molecule's biological activity while affording, for example, increased solubility or specifically reactive functional groups will also be useful in the practice of the present invention.

EXAMPLE 1
Preparation of Glycol Adduct of Amiloride

By way of illustrative example, 1 g of amiloride is dissolved in 50 ml of ethylene glycol. The pH is adjusted by addition of sufficient 1 N sodium hydroxide solution to maintain a pH of 9 for 5 hours. The pH is then changed to pH 5 by addition of dilute HCl. The adduct of amiloride with ethylene glycol is isolated by salting, extraction, washing and further purification if needed.

In like manner, but substituting propane-1,3-diol and other alkanediols of the formula $HO-(CH_2)_n-OH$ and $HO-C_nH_{2n}-OH$, where n is 3, 4, 5 or greater, there are produced the propylene glycol adduct and other alkanediol adducts of amiloride.

A preferred amiloride derivative is the ethylene glycol adduct of amiloride. This derivative, confirmed by NMR analysis, retains biological activity similar to that of the unmodified molecule. This and other adducts of amiloride may be linked to, for example, affinity gel support materials to form amiloride "affinity gels" having channel protein-binding activity. The discovery of such amiloride adduct derivatives and uses therefor are particularly important aspects of the present invention inasmuch as amiloride itself cannot be directly linked to an affinity gel or other support without loss of activity of the drug.

In addition, by virtue of their ability to bind to and block the transport activity of the channel protein, the above adducts, as well as amiloride derivatives and related derivative adducts may also be useful in directly treating disorders related to abnormal transport activity in membranes. For example, the materials are conceived to have useful diuretic activity when given orally and to be useful when applied topically for the prevention and treatment of glaucoma. In these uses, the materials may be formulated in vehicles standard for oral or ocular use and are given in amounts sufficient to affect aqueous transport but below amounts having toxic or irritating properties.

The amiloride affinity gels used in purifying the present $Na^+$ channel protein may be formed by covalently bonding the above amiloride ethylene glycol adduct or analogous amiloride adducts to a modified polysaccharide support, as for example a support derived from a purified agarose (e.g., Sepharose® (Pharmacia)), from an alpha-linked dextran (e.g., Sephadex® (Pharmacia)) or from cellulose. Short-chain saccharides, as for example glucose or dextrose, may also be used. Although such affinity purification compositions will be referred to herein as "affinity gels," when the polysaccharide is short or is not cross-linked the composition may not in fact be a typical gel.

Preparation of amiloride gels may be accomplished using a glycol linker group and CNBr by methods standard in the art. A preferred method involves the use of an ammonium salt, as for example $NH_4Cl$ or $(NH_4)_2SO_4$, to generate free ammonia species which derivatize the gel and allow rapid formation of reactive coupling species.

EXAMPLE 2
Preparation of Amiloride Affinity Gel

By way of illustrative example, 100 ml of agarose beads are washed with water, freed of interstitial water by suction filtration, and then added to 80 ml of water. To the suspension is then added an ammonium salt (for example, $NH_4Cl$ or $(NH_4)_2SO_4$) to a concentration of approximately 1 M. The pH is then increased to approximately 9, causing generation of "free ammonia" species. After about five minutes, a glycol adduct of amiloride, as for example, the ethylene glycol adduct, is added while maintaining the pH constant at 9 with NaOH. Reaction is continued until the pH remains constant. The mixture is then brought to a pH of about 4.5 and reduced with, e.g., sodium borohydride at 4° C. for 12 hours. The resulting amiloride gel is washed thoroughly to remove all reducing agent and dried by vacuum filtration. If desired, it may be further dried to a powder by drying under vacuum at 30°–60° C. The resultant gel or powder is useful as reagent to isolate the purified $Na^+$ channel. It is also useful when administered orally in producing diuresis, inhibiting gastric acid secretion and treating diarrhea. It is useful when applied topically in treating glaucoma.

EXAMPLE 3
Preparation of Amiloride Affinity Gel Using CNBr

Using procedures described in *Affinity Chromatography* by W. H. Scouten, pages 45–49 (John Wiley and Sons, 1981) and in *Affinity Chromatography* edited by P. D. G. Dean, W. S. Johnson and F. A. Middle (IRL Press, 1985), gels may also be produced from the ethylene glycol and other glycol adducts of amiloride and various polysaccharide gels, such as Sepharose®, Sephadex® and cellulose. In one such procedure, the support (Sepharose® 4B) is first reacted with ethylene glycol, using CNBr, to provide a spacer group. The glycol-Sepharose® is then reacted with amiloride at pH 9 for 5 hours. The pH is then lowered to 4.5 and sodium borohydride is added. The mixture is allowed to stir overnight at 4° C. The amiloride-Sepharose® is then washed extensively with Tris-HCl, Tris base, sodium bicarbonate and then water. The final product has a distinctive yellow color.

In the above examples, ethylene glycol may be replaced by other glycols, such as $HO-(CH_2)_n-OH$ and $HO-C_nH_{2n}-OH$ where n is a integer of from 3 to about 11, to afford the correspondingly-modified amiloride gels in which the linker adduct contains, for example, 3, 4, 5 or more carbon atoms.

In addition, agarose may be replaced by commercially available supports such as an alpha-linked dextran (e.g., Sephadex®), cellulose, simple sugars or complex carbohydrates to afford the corresponding gels containing the modified amiloride. Similar gels may be formed using short-chain polysaccharides or monosaccharides such as glucose or dextrose using the above methods or other methods standard in the art.

It will be noted that appropriate gels may be formed by reaction of a preformed amiloride adduct derivative with a gel material, by reaction of amiloride with a suitably prepared (i.e., linker group-primed) gel, or by simultaneous in situ reaction of amiloride, linker group and gel. Specific conditions and modifications to these procedures will also be recognized by those skilled in the art.

In addition, it will be apparent that support media other than materials commonly used for affinity gel purposes, as well as amiloride derivatives other than glycol adducts, will be useful in the practice of the present invention. For example, therapeutic benefits such as reduction of intraocular pressure attributable to amiloride may be enhanced by utilizing the present invention to bond amiloride to materials or functional groups which increase intraocular absorption or which lengthen intraocular residence time.

The above amiloride gel materials are useful in the isolation and purification of the $Na^+$ channel peptide and may also be used directly as therapeutic agents. The gel materials may be administered orally to human or animal subjects to inhibit gastric acid secretion and thus to treat or prevent gastric ulcer, to enhance diuresis and to prevent diarrhea, particularly diarrhea associated with cholera. Furthermore, such gel materials, especially when derived from short-chain saccharides such as glucose or dextrose, or from dextran, may be applied topically to the eye to reduce intraocular pressure, as for example to treat glaucoma.

The $Na^+$ channel peptide may be isolated and purified using the amiloride affinity gels described above following methods well known in the art, as discussed below.

EXAMPLE 4

Purification of Channel Peptide

By way of illustrative example, bovine kidney cortex cell membranes or bovine trachea apical cell membranes are collected and pooled until the pooled membranes contain about 100 mg of protein as determined by the Lowry method. The pooled membranes in 100 mM HEPES, pH 7.4, are centrifuged at 40,000 g for 30 minutes. The pelleted material was resuspended in 100 mM HEPES, pH 7.4, containing 3% sodium cholate (4.5–5.5 mg of membrane protein/3 ml of solution) containing in addition bacitracin (100 microgram/g), phenylmethylsulfonyl fluoride (0.5%) and iodoacetamide (1 mM). The mixture is chilled on ice for 60 minutes with occasional agitation, then centrifuged at 40,000 g for 30 minutes. The supernatant, containing the solubilized protein, may be purified immediately or frozen at −70° for later purification.

The solubilized protein preparation obtained from about 10 g of cell membrane is purified using 100 ml of the affinity gel described in Example 2. The protein solution and gel are stirred overnight in the cold. The gel is washed with 20 volumes of HEPES solution, pH 7.2, by filtration. The adsorbed protein is eluted with $10^{-3}$ M amiloride in dilute saline containing 0.5% cholate by stirring for two hours. The elution was repeated and the combined eluates are dialyzed against 100 mM HEPES/1% sodium cholate for one week in the cold, changing buffers once or twice a day. The residue is reapplied to the affinity gel and the batch purification process repeated. The resulting purified protein is then resubmitted to analysis and characterization. Typically, 10 g of cell membrane yields about 0.1 microgram of purified protein.

The purified protein was analyzed by gel filtration chromatography (Sepharose® CL-4B) and by SDS-polyacrylamide gel electrophoresis (SDS-PAGE). FIG. 1 shows a typical elution curve from a Sepharose® 4B column of crude tracheal membrane homogenate in 400 mM sucrose (top) and protein purified by the amiloride affinity gel (lower). Elution from the column (1.5×155 cm. i.d.) was at a flow rate of 0.3 ml/min. Fractions of 0.5 ml were collected and protein was determined as the optical absorbance at 280 nm ($A_{280}$).

The unexpectedly high absorbance for the protein peak appears to be due to bound detergent. Such detergent would act to "amplify" the elution signal, allowing measurement of smaller amounts of protein than would be possible otherwise. However, the bound detergent also interferes with the accurate determination of molecular weight. Present data suggests that the molecular weight of the isolated channel protein is approximately 200–220 kD.

Figure 2:
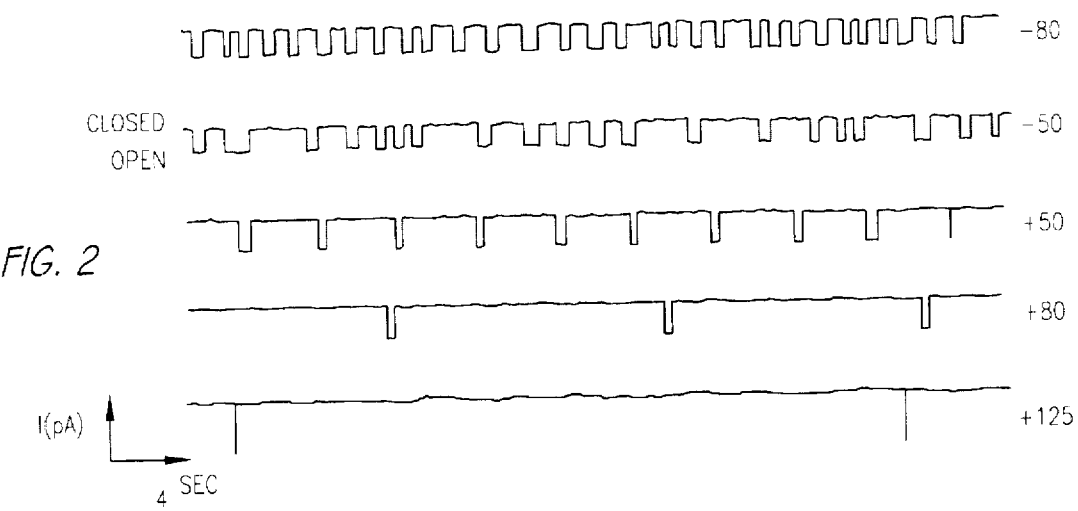
FIG. 2 is a depiction of typical single-channel recording tracings obtained for the $Na^+$ channel protein at potentials ranging from −80 to +125 mV.

Typical channel recordings obtained at potentials ranging from −80 to +125 mV in a reconstituted lipid bilayer system are shown in FIG. 2. At the most positive potentials (equivalent to negative cell potentials under the electrophysiological convention), the channel was essentially closed with an occasional short opening seen sporadically. With depolarization, the channel was seen to be open with increasing probability. However, even at highly depolarized potentials (−80 mV), the channel exhibited frequent closings. At potentials greater than −150 mV (physiologically unrealistic), the channel was found to be essentially in the open state. Further studies appear necessary to characterize the opening probabilities and gating potentials in a definitive manner.

Figure 3:
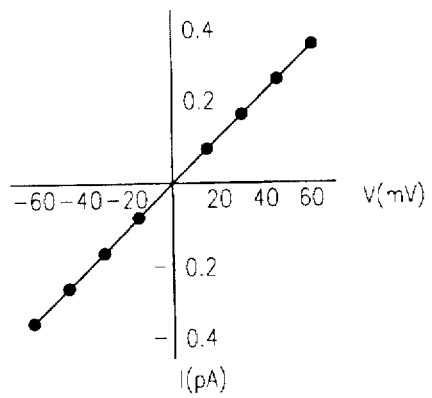
FIG. 3. is a graph representing an i-V curve for the $Na^+$ channel protein, derived from typical single-channel recording data.

The single-channel data typified by FIG. 2 yields the i-V curve in FIG. 3, which shows a conductance of 5–7 pS, somewhat higher than that found for the channel protein from crude membrane preparations.

Under bi-ionic conditions, the $Na^+/K^+$ selectivity ratio of the channel protein was greater than 100. The isolated channel exhibited half-saturation at about 90 mM $Na^+$.

The effect of amiloride on sodium concentration has been studied. The purified channel was found to be extremely amiloride sensitive, with an $IC_{50}$ of about 0.07 micromolar.

In both the crude membrane preparation and in purified channel preparations, a $pH/Ca^{++}$ effect was apparent in that activity was not seen in unbuffered, acidic solutions. Buffering to pH 7.2 elicited the channel activity. While this effect, in the main, is most likely due to a pH effect, the concomitant changes in free $Ca^{++}$ may also contribute.

EXAMPLE 5

Transport Electrical Properties of the Protein Channel

The electrical properties of the purified protein were studied by first chromatographing it on Sephadex® G-150 and then reconstituting the void volume into lipid bilayers (phosphatidylethanolamine/phosphatidylcholine=4/1) formed by sonication dialysis (Coronado, et al., Biophys. J., Vol. 43, pp. 231–236 (1983)). The microelectrode (i.d.=1 micrometer) and the external bath contained 0.5 M sodium citrate, Na sodium gluconate or potassium gluconate. All contained 1 mM $CaCl_2$ and 5 mM Tris, pH 7.4. Amiloride could be included. The currents were discrete and fluctuating with a unitary-channel conductance of 6 pS.

Typical channel recordings obtained at potentials ranging from −80 to +125 mV are shown in FIG. 2.

The data obtained for trachea epithelial preparations is summarized in Table I, which shows results for both the purified reconstituted channel protein and for the crude membrane preparation.

TABLE I

COMPARISON OF CHANNEL PROPERTIES

|  | PURIFIED | MEMBRANE |
| --- | --- | --- |
| Conductance (pS) | 5–7 | 2–3 |
| Saturation (mM) | 90 | 85 |
| $Na^+$ selectivity | 100 | 100 |
| Amiloride, $IC_{50}$ (micromolar) | .07 | .1 |
| $pH/Ca^{++}$ | + | + |

The results which have been obtained for the isolated purified airway epithelium sodium channel compare favorably with those reported for $Na^+$ channels in the natural state in other tissues. Palmer, L., *J. Membrane Biol.*, Vol. 96, pp. 97–106 (1987). In particular, both the channel conductance and its selectivity suggest its identification as the epithelial $Na^+$ channel. This conclusion is strengthened by the protein's high sensitivity to amiloride.

The $Na^+$ peptide channel disclosed herein may be used in methods now standard in the art to produce polyclonal or monoclonal antibodies thereto. These antibodies may be used in accordance with standard immunofluorescence or radioimmunoassay techniques to produce diagnostic assays capable of determining, in histopathological samples, the extent to which volume and pressure problems may result from abnormally high or abnormally low presence of the peptide channel in appropriate membranes. Alternately, radio-labeled or fluorescent-labeled derivatives of amiloride, as for example derivatives labeled on ligand adducts such as the glycol adducts described herein, may be used to quantitate the presence of the channel protein.

The purified $Na^+$ channel may also be used in conjunction with, for example, radio-labeled amiloride in a screening procedure capable of evaluating the ability of new chemical entities to displace the amiloride. Entities that displace the bound labeled channel blocker may be presumed to affect volume and pressure control mechanisms in humans and other animals and are therefore candidates for further in vivo evaluation. The present $Na^+$ channel peptide is thus useful in providing an in vitro assay methodology capable of screening large numbers of test compounds without requiring the use of large numbers of experimental animals. The methods to be employed in such screening assays are well known to those skilled in the art given the present disclosure.

Given the disclosure of the present invention, it will be apparent to those skilled in the art that various modifications and equivalents to the embodiments described herein will be possible. It is not intended that the scope of the present invention be limited except as by the appended claims.

What is claimed is:

1. A glycol adduct of amiloride produced by the reaction of covalently bonding amiloride with an alkanediol of the formula $HO-(CH_2)_n-OH$ or $HO-C_nH_{2n}-OH$, wherein n is an integer of from 2 to 11.

2. The glycol adduct of amiloride of claim 1 wherein said alkanediol is ethylene glycol.

3. A composition formed by contacting amiloride with an alkanediol of the formula $HO-(CH_2)_n-OH$ or $HO-C_nH_{2n}-OH$, wherein n is an integer of from 2 to 11, in the presence of a base, whereby the amiloride is covalently bonded to the alkanediol.

4. A reaction mixture as in claim 3 wherein the base is sodium hydroxide.

5. A reaction mixture as in claim 3 wherein the composition is further contacted with an acid.

6. A composition as in claim 5 wherein the acid is hydrochloride acid.

7. A composition of claim 3 wherein the alkanediol is ethylene glycol.

8. A composition of claim 5 wherein the alkanediol is ethylene glycol.

* * * * *